(12) United States Patent
Kuad et al.

(10) Patent No.: US 9,040,724 B2
(45) Date of Patent: May 26, 2015

(54) DIARYL SULFONE COMPOUND, AND MANUFACTURING METHOD FOR SAME

(75) Inventors: Paul Kuad, Mulhouse (FR); Hisaaki Kanda, Hyogo (JP); Takeshi Fujiwara, Hyogo (JP); Hiroyuki Shiraishi, Hyogo (JP)

(73) Assignee: SUMITOMO SEIKA CHEMICALS CO., LTD., Kako-Gun (JP)

(*) Notice: Subject to any disclaimer, the term of this patent is extended or adjusted under 35 U.S.C. 154(b) by 0 days.

(21) Appl. No.: 13/583,725

(22) PCT Filed: Mar. 9, 2011

(86) PCT No.: PCT/JP2011/055452
§ 371 (c)(1),
(2), (4) Date: Sep. 10, 2012

(87) PCT Pub. No.: WO2011/114954
PCT Pub. Date: Sep. 22, 2011

(65) Prior Publication Data
US 2013/0005993 A1  Jan. 3, 2013

(30) Foreign Application Priority Data

| Mar. 18, 2010 | (JP) | 2010-062865 |
| Mar. 18, 2010 | (JP) | 2010-062875 |
| Mar. 19, 2010 | (JP) | 2010-064011 |
| Mar. 19, 2010 | (JP) | 2010-064031 |

(51) Int. Cl.
| C07C 323/65 | (2006.01) |
| C07C 327/06 | (2006.01) |
| C07D 331/02 | (2006.01) |
| C07C 319/06 | (2006.01) |

(52) U.S. Cl.
CPC .............. *C07C 323/65* (2013.01); *C07C 327/06* (2013.01); *C07D 331/02* (2013.01); *C07C 319/06* (2013.01)

(58) Field of Classification Search
CPC .................................................. C07C 323/65
USPC ........................................................ 549/90
See application file for complete search history.

(56) References Cited

U.S. PATENT DOCUMENTS

| 4,808,696 A | 2/1989 | Takekoshi et al. |
| 5,183,917 A | 2/1993 | Maruyama |
| 2003/0218154 A1 | 11/2003 | Sasaki ......................... 252/582 |
| 2008/0200582 A1 | 8/2008 | Craciun et al. |
| 2009/0163683 A1 | 6/2009 | Kim |
| 2010/0076106 A1 | 3/2010 | Iwasa |
| 2010/0109317 A1 | 5/2010 | Hoffmueller et al. |

FOREIGN PATENT DOCUMENTS

| CN | 101636276 | 1/2010 |
| JP | 3-38564 A | 2/1991 |
| JP | H3-109368 | 5/1991 |
| JP | 3-153664 A | 7/1991 |
| JP | 8143532 A | 6/1996 |
| JP | 8143533 | 6/1996 |
| JP | H9-3058 | 1/1997 |
| JP | 940636 A | 2/1997 |
| JP | 2785876 | 5/1998 |
| JP | 2003-176332 A1 | 6/2003 |
| JP | 2003-292541 A | 10/2003 |
| JP | 2004-176006 | 6/2004 |
| JP | 2007-304154 | 11/2007 |
| JP | 2008-197239 | 8/2008 |
| JP | 2009-102550 A1 | 5/2009 |
| JP | 2009-120832 A1 | 6/2009 |
| JP | 2009-149649 A1 | 7/2009 |
| JP | 2010-97195 A1 | 4/2010 |
| JP | 2010-135652 A1 | 6/2010 |
| SU | 499261 | 2/1974 |
| SU | 802275 A1 | 2/1981 |
| SU | 1421736 A1 | 9/1988 |

(Continued)

OTHER PUBLICATIONS

King, Med. Chem., Principle and Practice (1994), pp. 206-208.*
Notification of the First Office Action issued Jun. 28, 2013 from The State Intellectual Property Office of the Peoples Republic of China in counterpart application No. 201180014496.2 with English translation.
Supplementary European Search Report dated Aug. 6, 2013 issued in counterpart application No. 11756144.9.
Supplementary European Search Report dated Aug. 6, 2013 issued in counterpart application No. 11756143.1.
Yasuo Suzuki et al.: "Synthesis of Highly Refractive and Transparent Polyimides Derived from 4,4'-[p-Sulfonylbis (phenylenesulfanyl)] diphthalic Anhydride and Various Sulfur-containing Armatic Diamines", Polymer Journal, vol. 40, No. 5, Jan. 1, 2008, pp. 414-420.

(Continued)

*Primary Examiner* — Taofiq A Solola
(74) *Attorney, Agent, or Firm* — Kratz, Quintos & Hanson, LLP

(57) ABSTRACT

The present invention provides a diaryl sulfone compound represented by Formula (1) below:

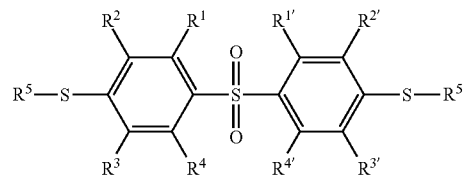

wherein $R^1$ to $R^4$ and $R^{1'}$ to $R^{4'}$ are the same or different; each represents hydrogen, $C_{1-4}$ alkyl, or halogen; and $R^5$ is (thio) glycidyl, acryloyl, or the like; and a method for producing the same.
According to the present invention, a novel compound useful as a monomer for producing synthetic resin having a high refractive index and excellent transparency for optical materials can be efficiently produced with a simple production process, using an inexpensive material as a starting material.

10 Claims, No Drawings

(56) References Cited

FOREIGN PATENT DOCUMENTS

| WO | WO 90/04587 A1 |   | 5/1990 |
|----|----------------|---|--------|
| WO | 2008/098753    | * | 8/2008 |
| WO | 2008/101806    |   | 8/2008 |

OTHER PUBLICATIONS

High Performance Polymer Optical Material, Edition 1, Aug. 2005, pp. 31-35.
American Review of Tuberculosis, vol. 54, 1946, pp. 295-298.
Journal of Functional Materials, vol. 39, Issue 3, 2008, pp. 460-464.
International Search Report for International Application No. PCT/JP2011/055452 dated Apr. 19, 2011.
U.S. Office Action dated May 21, 2013 issued in (U.S. Appl. No. 13/583,730).
U.S. Appl. No. 13/583,730.
Charmas, Wladyslaw, et al., "Thioether Glycidyl Resins. VII, Products of Condensation of Bis(4-Mercaptophenyl) Sulfide and Bis(4-Mercaptophenyl) Sulfone with Epichlorohydrin," Journal of Applied of Polymer Science, vol. 39 (1990), pp. 1623-1633.
English Translation of the Office Action Issued in the Corresponding JP Patent Application No. 2011-050045, on Jan. 6, 2015.
Office Action Issued in the Corresponding U.S. Appl. No. 13/583,730, on Mar. 24, 2015.
STN/CAS online results JP 2009067938, Liu et al. (2009), cited in the Office Action dated Mar. 24, 2015 for the corresponding U.S. Appl. No. 13/583,730.

* cited by examiner

DIARYL SULFONE COMPOUND, AND MANUFACTURING METHOD FOR SAME

TECHNICAL FIELD

The present invention relates to a novel diaryl sulfone compound useful as a monomer for producing resin for organic optical materials, a method for producing the same, and a method for producing a starting compound used in the production method.

BACKGROUND ART

Because optical materials formed from synthetic resin are light compared to inorganic materials such as glasses, excellent in molding processability and the like, and easy to handle, such optical materials have been widely used in various applications in recent years. Polystyrene resin, polymethylmethacrylate resin, polycarbonate resin, diethylene glycol diallyl carbonate resin, and the like have been heretofore used as such resin for organic optical materials.

However, previous resins for organic optical materials are not always satisfactory because these resins have drawbacks such as a low refractive index, a high birefringence, a high dispersibility, and the like; and are also poor in heat resistance and shock resistance. In particular, diethylene glycol diallyl carbonate resin (CR-39) and the like used as lens materials have a low refractive index (1.50). Therefore, when these resins are used as lenses, the edge thickness and the central thickness become thick, causing drawbacks such as degradation in the appearance of the lenses and an increase in the weight.

Consequently, attempts have been made to improve the refractive index of resin for organic optical materials. For example, as a monomer for producing resin having a high refractive index and excellent transparency, Patent Literature 1 and Patent Literature 2 listed below disclose a diaryl sulfide compound represented by the following chemical formula (a):

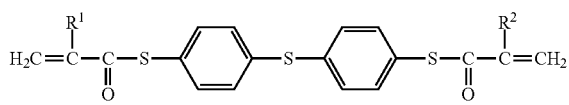

wherein $R^1$ and $R^2$ are hydrogen or methyl.

Likewise, as a monomer for producing resin having a high refractive index and excellent transparency, Patent Literature 3 listed below also discloses a diaryl sulfide compound represented by the following chemical formula (b):

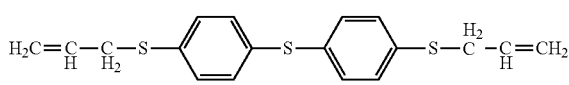

While these diaryl sulfide compounds are described as monomers for producing resin having a high refractive index and excellent transparency, the production of these compounds requires a 4,4'-dimercaptodiaryl sulfide compound, which is an expensive compound represented by the following chemical formula:

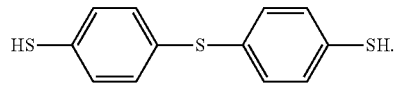 [SMILES: Sc1ccc(Sc2ccc(S)cc2)cc1]

Accordingly, the diaryl sulfide compounds of the above chemical formulae (a) and (b) obtained using the above-mentioned compound as a starting material are costly, and the economic efficiency thereof is low. Therefore, there is a demand for a less-expensive material as a monomer that can be used for producing resin having a high refractive index and excellent transparency.

CITATION LIST

Patent Literature

PLT 1: WO1990/04587
PLT 2: Japanese Unexamined Patent Publication No. H03-109368
PLT 3: Japanese Unexamined Patent Publication No. H09-3058

SUMMARY OF INVENTION

Technical Problem

The present invention was made in light of the current situation of the conventional techniques. A main object of the present invention is to provide, as a monomer for producing synthetic resin having a high refractive index and excellent transparency, a compound that is less expensive compared to conventional compounds and that has performance at least equivalent to that of conventional compounds. The present invention also provides a method for producing the compound.

Further, another object of the present invention is to provide a method for producing a starting compound used in the above-described method for producing the novel compound, with low environmental impact and under economically advantageous conditions.

Solution to Problem

The present inventors conducted extensive studies to achieve the above-described objects, and as a result, found that a novel diaryl sulfone compound having a specific substituent has excellent performance as a monomer that can be used for producing resin having a high refractive index, a high hardness, and good transparency. The present inventors also found that the diaryl sulfone compound can be easily produced under economically advantageous conditions by using a less-expensive substance, i.e., a dimercaptodiaryl sulfone compound, as a starting material.

Further, in regard to the dimercaptodiaryl sulfone compound as a starting material used in the above-described production method, the present inventors found that the compound can be simply produced with a less-expensive process by a method in which a dimethylthiodiaryl sulfone compound represented by a specific formula is used as a starting material to react with a halogenating agent, followed by hydrolysis.

The present invention was completed as a result of further studies based on these findings.

Specifically, the present invention provides the following novel diaryl sulfone compounds, method for producing the same, and method for producing a starting compound used in the production method.

Item 1. A diaryl sulfone compound represented by Formula (1):

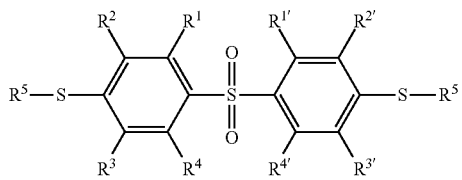

wherein $R^1$ to $R^4$ and $R^{1'}$ to $R^{4'}$ are the same or different, and each represents hydrogen, $C_{1-4}$ alkyl, or halogen; and $R^5$ is a group represented by the following formula:

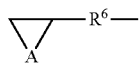

wherein $R^6$ represents $C_{1-4}$ alkylene, and A represents oxygen or sulfur; or a group represented by the following formula:

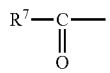

wherein $R^7$ represents $C_{2-5}$ alkenyl.

Item 2. The diaryl sulfone compound according to Item 1, represented by Formula (1-1):

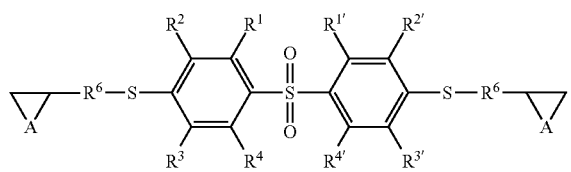

wherein $R^1$ to $R^4$ and $R^{1'}$ to $R^{4'}$ are the same or different, and each represents hydrogen, $C_{1-4}$ alkyl, or halogen; $R^6$ represents $C_{1-4}$ alkylene; and A represents oxygen or sulfur.

Item 3. The diaryl sulfone compound according to Item 1, represented by Formula (1-2):

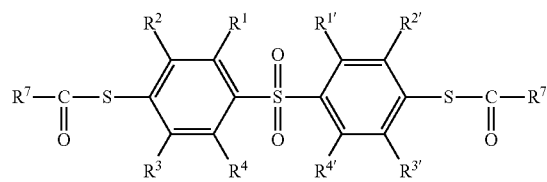

wherein $R^1$ to $R^4$ and $R^{1'}$ to $R^{4'}$ are the same or different, and each represents hydrogen, $C_{1-4}$ alkyl, or halogen; and $R^7$ represents $C_{2-5}$ alkenyl.

Item 4. The diaryl sulfone compound according to any one of Items 1 to 3, wherein $R^1$ to $R^4$ and $R^{1'}$ to $R^{4'}$ are all hydrogen.

Item 5. A method for producing a diaryl sulfone compound represented by Formula (1-1-a):

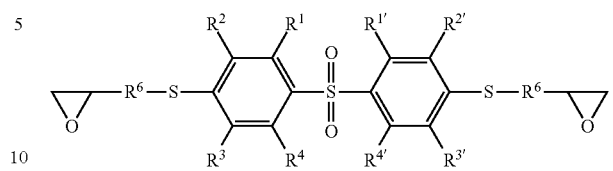

wherein $R^1$ to $R^4$ and $R^{1'}$ to $R^{4'}$ are the same or different, and each represents hydrogen, $C_{1-4}$ alkyl, or halogen; and $R^6$ is $C_{1-4}$ alkylene;

the method comprising reacting a 4,4'-dimercaptodiaryl sulfone compound represented by Formula (2):

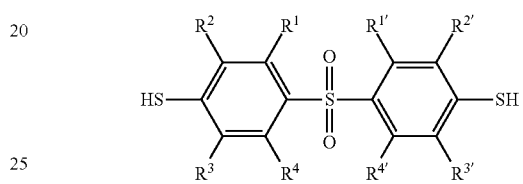

wherein $R^1$ to $R^4$, $R^{1'}$ to $R^{4'}$, and $R^6$ are as defined above,
with a halide represented by Formula (3):

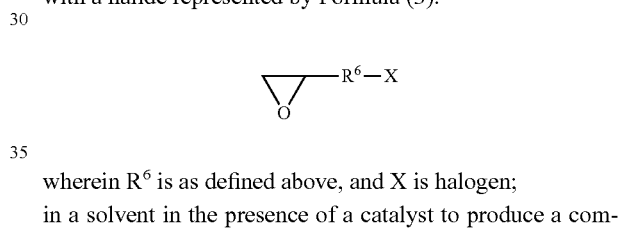

wherein $R^6$ is as defined above, and X is halogen;
in a solvent in the presence of a catalyst to produce a compound represented by Formula (4):

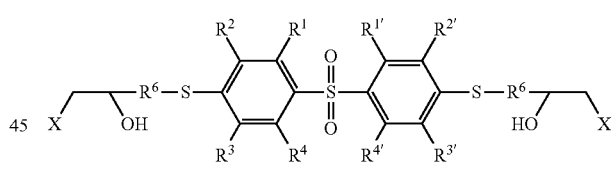

wherein $R^1$ to $R^4$, $R^{1'}$ to $R^{4'}$, $R^6$, and X are as defined above; and reacting the resulting compound with a base to perform a dehydrohalogenation reaction.

Item 6. A method for producing a diaryl sulfone compound represented by Formula (1-1-b):

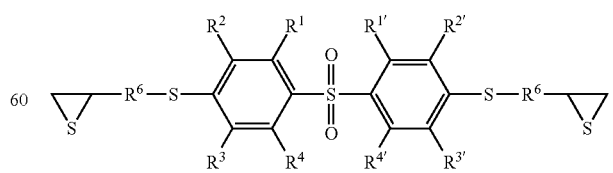

wherein $R^1$ to $R^4$ and $R^{1'}$ to $R^{4'}$ are the same or different, and each represents hydrogen, $C_{1-4}$ alkyl, or halogen; and $R^6$ represents $C_{1-4}$ alkylene;

the method comprising reacting a compound represented by Formula (1-1-a):

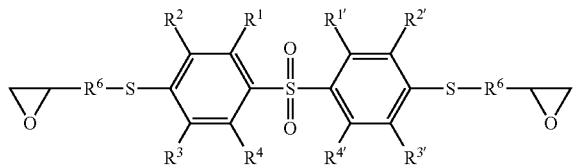

wherein $R^1$ to $R^4$, $R^{1'}$ to $R^{4'}$, and $R^6$ are as defined above; with at least one compound selected from the group consisting of thiourea and thiocyanates, in an organic solvent.

Item 7. A method for producing a diaryl sulfone compound represented by Formula (1-2):

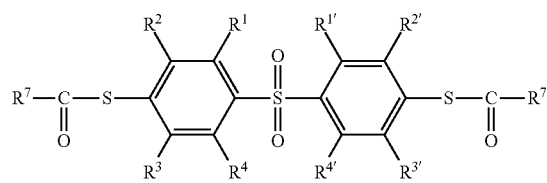

wherein $R^1$ to $R^4$ and $R^{1'}$ to $R^{4'}$ are the same or different, and each represents hydrogen, $C_{1-4}$ alkyl, or halogen; and $R^7$ represents $C_{2-5}$ alkenyl;

the method comprising reacting a salt of 4,4'-dimercaptodiaryl sulfone represented by Formula (2-1):

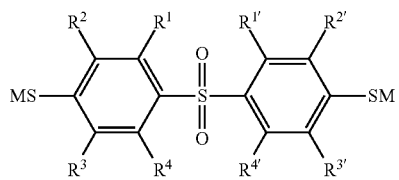

wherein $R^1$ to $R^4$, $R^{1'}$ to $R^{4'}$, and $R^7$ are as defined above; and M represents a cation moiety of a base;

with a halide represented by Formula (5):

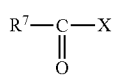

wherein $R^7$ is defined as above, and X represents halogen.

Item 8. A method for producing a dimercaptodiaryl sulfone compound represented by Formula (2):

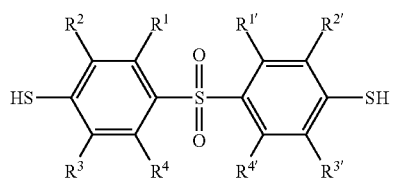

wherein $R^1$ to $R^4$ and $R^{1'}$ to $R^{4'}$ are the same or different, and each represents hydrogen, $C_{1-4}$ alkyl, or halogen;

the method comprising reacting a dimethylthiodiaryl sulfone compound represented by Formula (6):

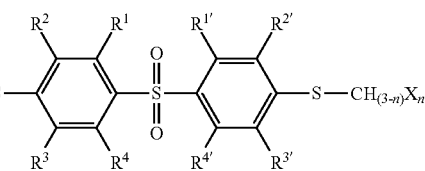

wherein $R^1$ to $R^4$ and $R^{1'}$ to $R^{4'}$ are as defined above; with a halogenating agent to obtain a diaryl sulfone compound represented by Formula (7):

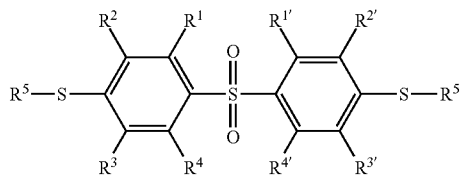

wherein $R^1$ to $R^4$ and $R^{1'}$ to $R^{4'}$ are as defined above; X represents halogen; and m and n each represents an integer of 1 to 3;

and subsequently subjecting the resulting compound to hydrolysis.

The novel diaryl sulfone compounds of the present invention and the method for producing the same are specifically described below.

Novel Diaryl Sulfone Compound

The diaryl sulfone compounds of the present invention are novel compounds not disclosed in any literature, and are represented by the following Formula (1):

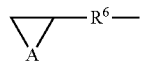

wherein $R^1$ to $R^4$ and $R^{1'}$ to $R^{4'}$ are the same or different, and each represents hydrogen, $C_{1-4}$ alkyl, or halogen; and $R^5$ is a group represented by the following formula:

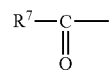

wherein $R^6$ represents $C_{1-4}$ alkylene; and A represents oxygen or sulfur; or a group represented by the following formula:

wherein $R^7$ represents $C_{2-5}$ alkenyl. The diaryl sulfone compound is a compound useful, for example, as a monomer that is used for producing synthetic resin for optical materials having a high refractive index and good transparency.

In the above Formula (1), examples of $C_{1-4}$ alkyl represented by $R^1$ to $R^4$ and $R^{1'}$ to $R^{4'}$ include linear or branched alkyl groups such as methyl, ethyl, n-propyl, isopropyl, n-butyl, sec-butyl, and tert-butyl, with methyl being particularly preferable. Examples of halogen include chlorine, bromine, iodine, and the like, with chlorine being particularly preferable.

Among the compounds represented by the above Formula (1), in the compound in which $R^5$ is a group represented by the following formula:

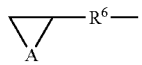

wherein $R^6$ represents $C_{1-4}$ alkylene; and A represents oxygen or sulfur;
in other words, in the compound represented by the following Formula (1-1):

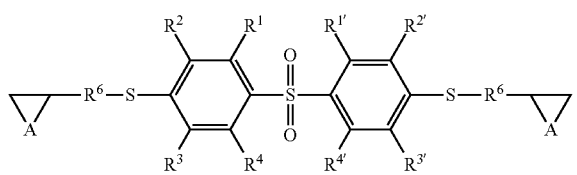

wherein $R^1$ to $R^4$, $R^{1'}$ to $R^{4'}$, $R^6$, and A are as defined above;
examples of $C_{1-4}$ alkylene represented by $R^6$ include linear alkylene groups such as methylene, ethylene, trimethylene, and tetramethylene; branched alkylene groups such as ethylethylene and 1,2-propylene; and the like.

Specific examples of the group represented by the formula:

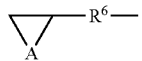

include glycidyl, thioglycidyl, and the like.

Specific preferable examples of the compounds represented by the above Formula (1-1) include a compound in which $R^1$ to $R^4$ and $R^{1'}$ to $R^{4'}$ are all hydrogen, $R^6$ is methylene, and A is O; a compound in which $R^1$ to $R^4$ and $R^{1'}$ to $R^{4'}$ are all hydrogen, $R^6$ is methylene, and A is S; and the like.

Among the compounds represented by the above Formula (1), in the compound in which $R^5$ is a group represented by the following formula:

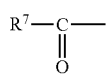

wherein $R^7$ represents $C_{2-5}$ alkenyl;
in other words, in the compound represented by the following Formula (1-2)

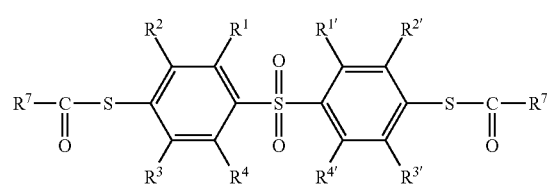

wherein $R^1$ to $R^4$, $R^{1'}$ to $R^{4'}$, and $R^7$ are as defined above;

$C_{2-5}$ alkenyl represented by $R^7$ is preferably linear or branched $C_{2-5}$ alkenyl having one or two carbon-carbon double bonds, and specific examples thereof include vinyl, allyl, isopropenyl, 1-butenyl, isobutenyl, and the like, with vinyl and isopropenyl being particularly preferable.

Specific preferable examples of the compound represented by the above Formula (1-2) include a compound in which $R^1$ to $R^4$ and $R^{1'}$ to $R^{4'}$ are all hydrogen, and $R^7$ is vinyl; a compound in which $R^1$ to $R^4$ and $R^{1'}$ to $R^{4'}$ are all hydrogen, and $R^7$ is isopropenyl; and the like.

Method for Producing Diaryl Sulfone Compounds (1) First Method

Of the diaryl sulfone compounds represented by Formula (1):

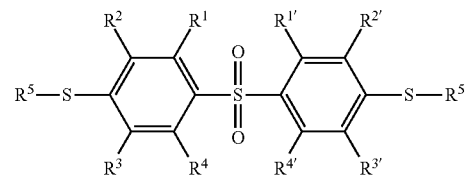

wherein $R^1$ to $R^4$, $R^{1'}$ to $R^{4'}$, and $R^5$ are as defined above;
the compound in which $R^5$ is a group represented by the following formula:

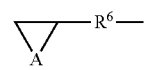

wherein $R^6$ and A are as defined above;
i.e., the diaryl sulfone compound represented by the following Formula (1-1):

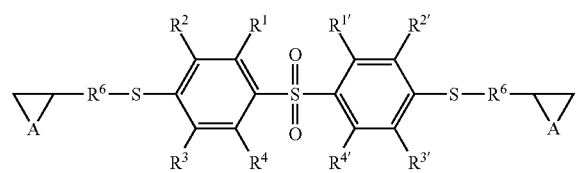

wherein $R^1$ to $R^4$, $R^{1'}$ to $R^{4'}$, $R^6$, and A are as defined above, can be produced by the method described below.

First, the compound represented by the above Formula (1-1) in which A is oxygen, i.e., the compound represented by the following Formula (1-1-a):

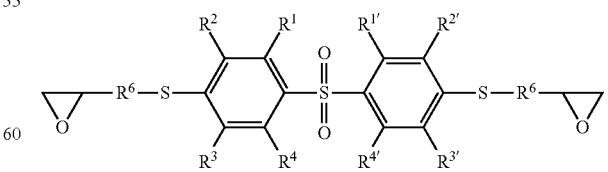

wherein $R^1$ to $R^4$, $R^{1'}$ to $R^{4'}$, and $R^6$ are as defined above;
can be obtained, for example, by reacting a 4,4'-dimercaptodiaryl sulfone compound represented by the following Formula (2):

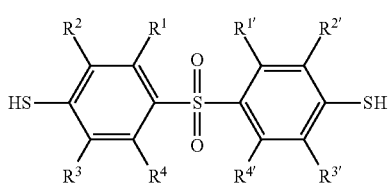

wherein $R^1$ to $R^4$ and $R^{1'}$ to $R^{4'}$ are as defined above;
with a halide represented by Formula (3):

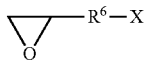

wherein $R^6$ is $C_{1-4}$ alkylene, and X is halogen;
in a solvent in the presence of a catalyst to obtain a compound represented by Formula (4):

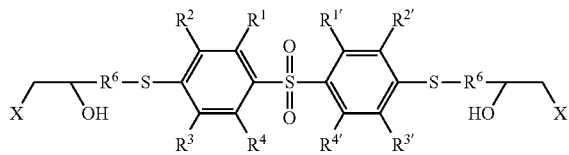

wherein $R^1$ to $R^4$, $R^{1'}$ to $R^{4'}$, $R^6$, and X are as defined above; and subsequently reacting the resulting compound with a base to perform a dehydrohalogenation reaction (HX elimination reaction).

The 4,4'-dimercaptodiaryl sulfone compound represented by the above Formula (2) is a known compound, and specific examples of $R^1$ to $R^4$ and $R^{1'}$ to $R^{4'}$ in the formula are the same as those in the above Formula (1). Specific examples of the 4,4'-dimercaptodiaryl sulfone compound include 4,4'-dimercaptodiphenyl sulfone, 3,3'-dimethyl-4,4'-dimercaptodiphenyl sulfone, 2,2'-dimethyl-4,4'-dimercaptodiphenyl sulfone, 2,2'-dimethyl-3,3'-dimethyl-4,4'-dimercaptodiphenyl sulfone, and the like, with 4,4'-dimercaptodiphenyl sulfone being particularly preferable.

In the halide represented by Formula (3), specific examples of alkylene represented by $R^6$ are the same as those in the above Formula (1-1). Examples of halogen represented by X include chlorine, bromine, iodine, and the like, with chlorine being particularly preferable.

Specific examples of the halide represented by Formula (3) include epichlorohydrin, epibromohydrin, and the like, with epichlorohydrin being particularly preferable.

The halide represented by Formula (3) is preferably used in an amount of about 2 to 10 mol, more preferably about 2 to 2.4 mol, per mole of the 4,4'-dimercaptodiaryl sulfone compound represented by Formula (2).

Examples of catalysts that may be used include lithium salts such as lithium chloride and lithium bromide, with lithium chloride being particularly preferable in view of the reactivity and the economic efficiency. The amount of catalyst used is preferably about 0.001 to 0.2 mol, more preferably about 0.01 to 0.1 mol, per mole of the 4,4'-dimercaptodiaryl sulfone compound represented by Formula (2).

Organic solvents are preferably used as the solvents in the reaction between the 4,4'-dimercaptodiaryl sulfone compound represented by Formula (2) and the halide represented by Formula (3). Examples of organic solvents include hydrocarbons such as n-hexane, n-heptane, cyclohexane, toluene, and xylene; halogenated hydrocarbons such as chlorobenzene and o-dichlorobenzene; alcohols such as methanol, ethanol, and isopropanol; and the like. It is particularly preferable to use toluene, methanol, and the like.

The specific reaction method is not particularly limited. Generally, the 4,4'-dimercaptodiaryl sulfone compound represented by Formula (2) and the halide represented by Formula (3) are uniformly mixed in the above-described solvent in the presence of a catalyst. The order of addition of each component is not particularly limited. Any method can be employed.

The concentration of the 4,4'-dimercaptodiaryl sulfone compound in the reaction solution is preferably about 1 to 30% by weight, and more preferably about 5 to 15% by weight.

The reaction temperature is not particularly limited, but it is preferably about 0 to 70° C., and more preferably about 30 to 60° C.

The reaction time is, for example, about 0.5 to 20 hours.

The above-described method can produce a compound represented by Formula (4):

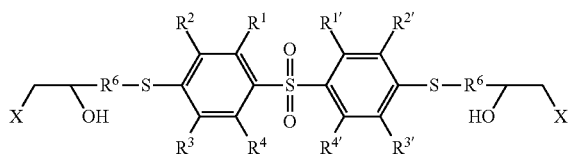

wherein $R^1$ to $R^4$, $R^{1'}$ to $R^{4'}$, $R^6$, and X are as defined above.

Next, the thus-obtained compound of Formula (4) is reacted with a base to perform a dehydrohalogenation reaction (HX elimination reaction), thereby obtaining the compound of Formula (1-1) in which A is oxygen, i.e., the compound represented by Formula (1-1-a):

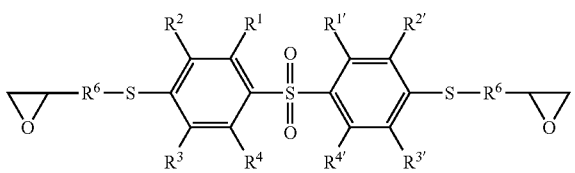

wherein $R^1$ to $R^4$, $R^{1'}$ to $R^{4'}$, and $R^6$ are as defined above.

The compound of Formula (4) obtained by the reaction at the first stage may be subsequently used for reaction with a base in a dissolved state in the reaction solvent after the reaction at the first stage; or the compound of Formula (4) may be separated from the solvent used for the reaction and then reacted with a base.

Examples of usable bases in the reaction with the compound of Formula (4) include metal hydroxides such as sodium hydroxide and potassium hydroxide; metal carbonates such as sodium carbonate and potassium carbonate; metal hydrides such as sodium hydride and potassium hydride; and the like. Sodium hydroxide is preferable in view of the reactivity and the economic efficiency.

The amount of base used is preferably about 0.1 to 10 mol, more preferably about 2.0 to 2.4 mol, per mole of the compound of Formula (4).

The reaction of the compound of Formula (4) with a base is usually performed by mixing these compounds in a solvent. Examples of solvents that can be used include organic solvents, solvent mixtures consisting of water and an organic solvent, and the like. As an organic solvent, the same solvent that is usable in the reaction at the first stage can be used.

When a solvent mixture of water and an organic solvent is used, the amount of water used is preferably about 0.1 to 100 parts by weight per part by weight of the organic solvent.

The concentration of the compound of Formula (4) in the reaction solution is preferably about 1 to 30% by weight, and more preferably about 10 to 20% by weight.

When a solvent mixture of water and an organic solvent is used, the reaction is preferably carried out in the presence of a phase-transfer catalyst. Examples of usable phase-transfer catalysts include tetrabutylammonium bromide, tetramethylammonium bromide, tetrabutylammonium tetrafluoroborate, and the like. Tetrabutylammonium bromide is particularly preferable in view of the reactivity and the economic efficiency. The amount of phase-transfer catalyst used is preferably about 0.001 to 0.1 mol, more preferably about 0.03 to 0.07 mol, per mole of the compound of Formula (4).

The reaction temperature is preferably about 0 to 70° C., and more preferably about 30 to 60° C.

The reaction time is, for example, about 0.5 to 20 hours.

In the case where a solvent mixture was used, after the reaction, the organic layer and the aqueous layer are separated by liquid-liquid separation, the organic layer is washed with water, and the solvent is distilled off. In this way, the diaryl sulfone compound represented by the above Formula (1-1-a) can be obtained. In the case where an organic solvent is used, water is added to the resulting product after the reaction is completed, and then the desired compound of Formula (1-1-a) can be easily separated in a manner similar to that described above for the case of a solvent mixture.

(2) Second Method

A compound of Formula (1-1) in which A is sulfur, i.e., a compound represented by Formula (1-1-b):

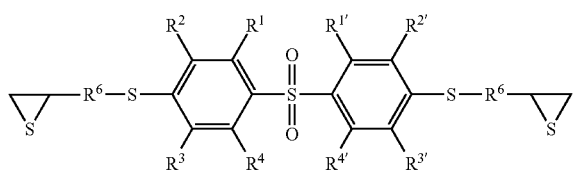

wherein $R^1$ to $R^4$, $R^{1'}$ to $R^{4'}$, and $R^6$ are as defined above; can be obtained by reacting the compound represented by the above (1-1-a):

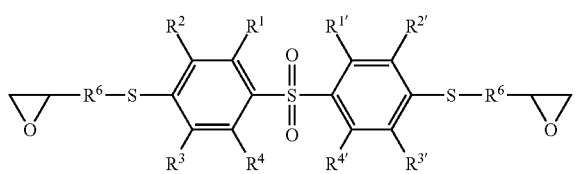

wherein $R^1$ to $R^4$, $R^{1'}$ to $R^{4'}$, and $R^6$ are as defined above; with at least one compound selected from the group consisting of thiourea and thiocyanates, in an organic solvent.

Examples of usable thiocyanates include potassium, thiocyanate, ammonium thiocyanate, and the like. Thiourea and thiocyanates may be used singly, or in a combination of two or more types thereof.

At least one compound selected from the group consisting of thiourea and thiocyanates is preferably used in an amount of about 2 to 8 mol, more preferably about 2 to 6 mol, per mole of the compound represented by Formula (1-1-a).

Examples of organic solvents include halogenated hydrocarbons such as methylene chloride, 1,2-dichloroethane, chlorobenzene, and o-dichlorobenzene; hydrocarbons such as n-hexane, n-heptane, cyclohexane, toluene, and xylene; ethers such as tetrahydrofuran and 1,4-dioxane; and alcohols such as methanol, ethanol, and isopropanol. The concentration of the compound represented by Formula (1-1-a) in the reaction solution is preferably about 1 to 30% by weight, and more preferably about 5 to 15% by weight.

The reaction temperature is preferably about 0 to 80° C., and more preferably about 10 to 60° C.

The reaction time may be, for example, about 0.5 to 20 hours.

After the reaction, water is added to the resulting product to separate the organic layer and the aqueous layer by liquid-liquid separation, the organic layer is washed with water, and then the solvent is distilled off. In this way, it is possible to obtain a desired diaryl sulfone compound represented by the following Formula (1-1-b):

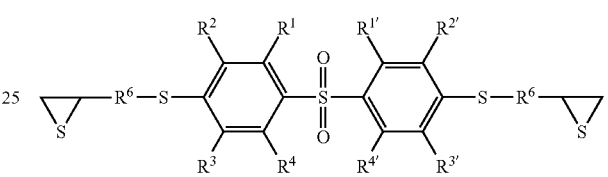

wherein $R^1$ to $R^4$, $R^{1'}$ to $R^{4'}$, and $R^6$ are as defined above.

(3) Third Method

Of the diaryl sulfone compounds represented by Formula (1):

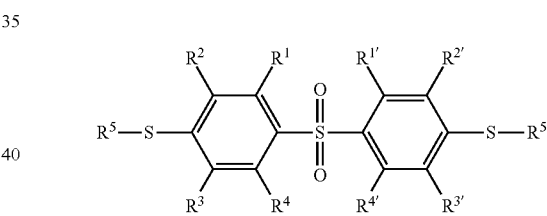

wherein $R^1$ to $R^4$, $R^{1'}$ to $R^{4'}$, and $R^5$ are as defined above; a compound in which $R^5$ is a group represented by the following formula

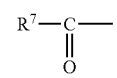

wherein $R^7$ represents $C_{2-5}$ alkenyl; i.e., a compound represented by the following Formula (1-2):

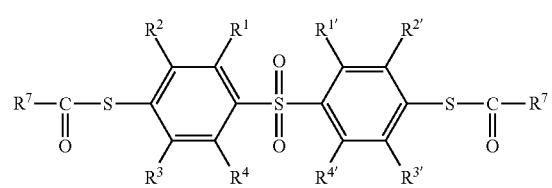

wherein $R^1$ to $R^4$, $R^{1'}$ to $R^{4'}$, and $R^7$ are as defined above; can be produced by the method described below.

For example, a salt of 4,4'-dimercaptodiaryl sulfone represented by the following Formula (2-1):

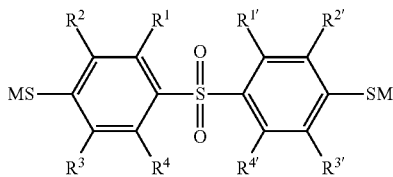

wherein $R^1$ to $R^4$ and $R^{1'}$ to $R^{4'}$ are as defined above, and M represent a cation moiety of a base;
is reacted with a halide represented by Formula (5):

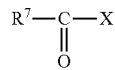

wherein $R^7$ represents $C_{2-5}$ alkenyl, and X represents halogen. In this way, the compound represented by the above Formula (1-2) can be obtained.

The salt of 4,4'-dimercaptodiaryl sulfone represented by the above Formula (2-1) can be obtained by reacting a 4,4'-dimercaptodiaryl sulfone compound represented by the following Formula (2):

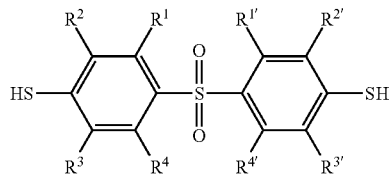

wherein $R^1$ to $R^4$ and $R^{1'}$ to $R^{4'}$ are as defined above; with a base.

Specific examples of the 4,4'-dimercaptodiaryl sulfone compound represented by the above Formula (2) are the same as those of the compound of Formula (2) described in the first method.

Examples of bases include metal hydroxides such as sodium hydroxide and potassium hydroxide; metal carbonates such as sodium carbonate and potassium carbonate; tertiary amines such as triethylamine and tributylamine; and metal hydrides such as sodium hydride and potassium hydride. Sodium hydroxide or sodium hydride is particularly preferable in view of the reactivity and the economic efficiency.

In the case where these bases are used, in the salt of 4,4'-dimercaptodiaryl sulfone represented by the above Formula (2-1), the cation moiety represented by M is a cation moiety that corresponds to the base used. For example, when represented by $M^+$, $M^+$ is $Na^+$, $K^+$, $N^+R_3H$, wherein R is alkyl such as ethyl or butyl, or the like.

The reaction of the 4,4'-dimercaptodiaryl sulfone compound represented by the above Formula (2) with a base can be usually performed by mixing these compounds in a solvent. Water or an organic solvent can be used as a solvent. Examples of organic solvents include hydrocarbons such as n-hexane, n-heptane, cyclohexane, toluene, and xylene; halogenated hydrocarbons such as chlorobenzene and o-dichlorobenzene; and aprotic polar solvents such as dimethylformamide, dimethylsulfoxide, and N-methylpyrrolidone.

When an organic solvent is used, non-aqueous bases such as tertiary amines and metal hydrides as described above are preferably used.

The amount of base used is preferably about 1 to 10 mol, more preferably about 2 to 2.4 mol, per mole of the 4,4'-dimercaptodiaryl sulfone compound.

The concentration of the 4,4'-dimercaptodiaryl sulfone compound in the solvent is preferably about 1 to 30% by weight, and more preferably about 5 to 15% by weight.

The reaction temperature for the reaction of the 4,4'-dimercaptodiaryl sulfone compound with a base is preferably about 0 to 70° C., and more preferably about 30 to 60° C.

The reaction time is, for example, about 0.5 to 20 hours.

Additionally, instead of obtaining the salt of 4,4'-dimercaptodiaryl sulfone represented by Formula (2-1) by reacting the 4,4'-dimercaptodiaryl sulfone compound represented by Formula (2) with a base by the above-described method, the salt of 4,4'-dimercaptodiaryl sulfone represented by Formula (2-1) may be purchased and used as is.

The reaction of the salt of 4,4'-dimercaptodiaryl sulfone represented by Formula (2-1) with a halide represented by Formula (5):

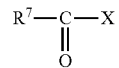

wherein $R^7$ and X are as defined above;
can be carried out in a solvent such as water, organic solvent, solvent mixture of water and an organic solvent, or the like. The same solvent that is usable in the reaction of 4,4'-dimercaptodiaryl sulfone compound represented by Formula (2) with a base can be used as an organic solvent.

For example, when the salt of 4,4'-dimercaptodiaryl sulfone represented by Formula (2-1) was obtained using water as a solvent by the above-described method, the halide represented by Formula (5) may be mixed as is in an aqueous solution containing the salt of 4,4'-dimercaptodiaryl sulfone; or a solution obtained by dissolving the halide represented by Formula (5) in an organic solvent may be mixed with an aqueous solution containing the salt of 4,4'-dimercaptodiaryl sulfone represented by Formula (2-1).

When the salt of 4,4'-dimercaptodiaryl sulfone represented by Formula (2-1) was obtained using an organic solvent as a solvent, the halide represented by Formula (5) may be mixed as is in the solvent; or a solution obtained by dissolving the halide represented by Formula (5) in the organic solvent may be added and mixed with the salt of 4,4'-dimercaptodiaryl sulfone.

Additionally, the 4,4'-dimercaptodiaryl sulfone compound represented by Formula (2), a base, and the halide represented by Formula (5) may be simultaneously added to an organic solvent for a reaction. In this case, it is assumed that, in the organic solvent, the 4,4'-dimercaptodiaryl sulfone compound represented by Formula (2) reacts with the base, thereby forming the salt of 4,4'-dimercaptodiaryl sulfone represented by Formula (2-1), and this resulting compound then reacts with the halide represented by Formula (5).

In the halide represented by Formula (5), specific examples of $C_{2-5}$ alkenyl represented by $R^7$ are the same as those in the above Formula (1-2). Examples of the halogen represented by X include chlorine, bromine, iodine, and the like, with chlorine being particularly preferable.

Specific examples of the halide represented by Formula (5) include acryloyl chloride, acryloyl bromide, methacryloyl chloride, and methacryloyl bromide, with acryloyl chloride, methacryloyl chloride, and the like being particularly preferable.

The halide represented by Formula (5) is preferably used in an amount of about 2 to 10 mol, more preferably about 2 to 2.4 mol, per mole of the salt of 4,4'-dimercaptodiaryl sulfone represented by Formula (2-1).

When the reaction of salt of 4,4'-dimercaptodiaryl sulfone represented by Formula (2-1) with the halide represented by Formula (5) is carried out in a solvent mixture of water and an organic solvent, the amount of water used is preferably about 0.1 to 100 parts by weight per weight part of the organic solvent. In the case where only an organic solvent is used, N-methylpyrrolidone is preferable. In the case where a solvent mixture of an organic solvent and water is used, a solvent mixture of toluene/cyclohexane/water is preferable.

The concentration of the salt of 4,4'-dimercaptodiaryl sulfone in the reaction solution is preferably about 1 to 30% by weight, and more preferably about 5 to 15% by weight.

The reaction temperature is not particularly limited, but is preferably about 0 to 70° C., and more preferably about 30 to 60° C.

The reaction time is, for example, about 0.5 to 20 hours.

When a solvent mixture was used, after the reaction, the organic layer and the aqueous layer are separated by liquid-liquid separation, the organic layer is washed with water, and the solvent is distilled off. In this way, it is possible to obtain the desired diaryl sulfone compound represented by the following Formula (1-2):

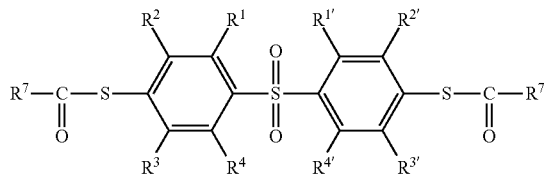

wherein $R^1$ to $R^4$, $R^{1'}$ to $R^{4'}$ and $R^7$ are as defined above. When water was used as a solvent, the desired diaryl sulfone compound of Formula (1-2) can be easily isolated by a method such as filtration.

Method for Producing 4,4'-Dimercaptodiaryl Sulfone Compound

The 4,4'-dimercaptodiaryl sulfone compound represented by Formula (2), which is used as a starting material in the above-described production of the diaryl sulfone compound, can be simply produced with a less-expensive process by a method comprising using the dimethylthiodiaryl sulfone compound represented by the following Formula (6) as a starting material to react it with a halogenating agent, and subsequently hydrolyzing the resulting product. This method is specifically described below.

(1) Step of Reacting Dimethylthiodiaryl Sulfone Compound with Halogenating Agent In the method of the present invention, as a first step, a dimethylthiodiaryl sulfone compound represented by the following Formula (6):

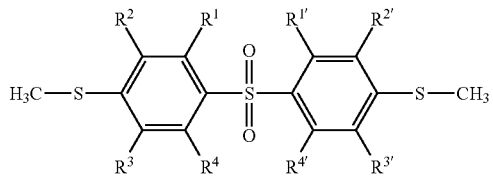

wherein $R^1$ to $R^4$ and $R^{1'}$ to $R^{4'}$ are the same or different, and each represents hydrogen, $C_{1-4}$ alkyl, or halogen, is reacted with a halogenating agent to obtain a diaryl sulfone compound represented by the following Formula (7):

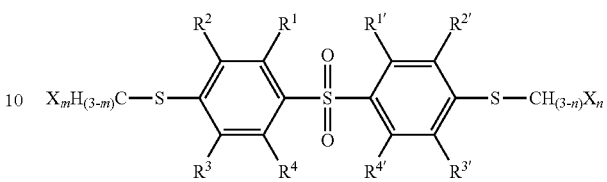

wherein $R^1$ to $R^4$ and $R^{1'}$ to $R^{4'}$ are as defined above; X represents halogen: and m and n each represents an integer of 1 to 3.

In Formula (6), specific examples of each of the groups represented by $R^1$ to $R^4$ and $R^{1'}$ to $R^{4'}$ are the same as those in the above Formula (1). Specific examples of the halogen represented by X include chlorine, bromine, iodine, and the like, with chlorine being preferable. Each of $R^1$ to $R^4$ and $R^{1'}$ to $R^{4'}$ is preferably hydrogen from an economic viewpoint.

Examples of halogenating agents include chlorine, sulfuryl chloride, phosphorus pentachloride, phosphorous trichloride, hypochlorous acid, bromine, and the like.

The amount of halogenating agent used is preferably about 2 to 12 mol, more preferably about 2 to 4 mol, per mole of the 4,4'-dimethylthiodiaryl sulfone compound represented by Formula (6).

In the reaction between the 4,4'-dimethylthiodiaryl sulfone compound and a halogenating agent, examples of reaction solvents that are preferably used include polar solvents such as dimethylsulfoxide, N-methylpyrrolidone, and N,N-dimethylformamide; halogenated hydrocarbons such as methylene chloride, 1,2-dichloroethane, chlorobenzene, and o-dichlorobenzene; hydrocarbons such as n-hexane, n-heptane, cyclohexane, toluene, and xylene; and the like. Toluene is more preferable from an economic viewpoint.

The amount of reaction solvent used is preferably about 10 to 5,000 parts by weight, more preferably about 100 to 1,000 parts by weight, relative to 100 parts by weight of the 4,4'-dimethylthiodiaryl sulfone compound.

The reaction temperature is preferably about 30 to 120° C., and more preferably about 40 to 70° C. The reaction time is usually about 1 to 30 hours.

The diaryl sulfone compound represented by Formula (7):

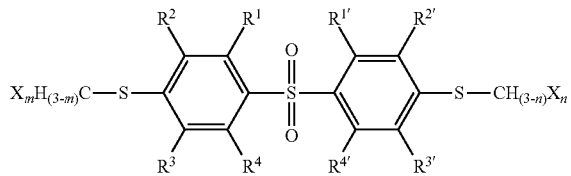

wherein $R^1$ to $R^4$, $R^{1'}$ to $R^{4'}$, X, m, and n are as defined above; can be obtained by the above-described method.

In the diaryl sulfone compound represented by the above Formula (7), the halogen represented by X corresponds to the halogenating agent used. Examples of the halogen include chlorine, bromine, iodine, and the like.

The values of m and n may vary in the range of 1 to 3. Usually, the values correspond to the amount of the halogenating agent used. For example, when the amount of halogenating agent is 2-fold moles of the 4,4'-dimethylthiodiaryl sulfone compound represented by Formula (6), the main product represented by Formula (7) is a diaryl sulfone compound in which the values of both m and n are 1. When the amount of halogenating agent is 4-fold moles of the 4,4'-dimethylthiodiaryl sulfone compound represented by Formula (6), the main product represented by Formula (7) is a diaryl sulfone compound in which the values of both m and n are 2.

The resulting diaryl sulfone can be obtained, if necessary, by water-washing and liquid-liquid separation. The diary sulfone compound can also be isolated with high purity by recrystallization after distilling off the solvent.

(2) Hydrolysis Step

Next, the diaryl sulfone compound obtained by the above step, which is represented by Formula (7):

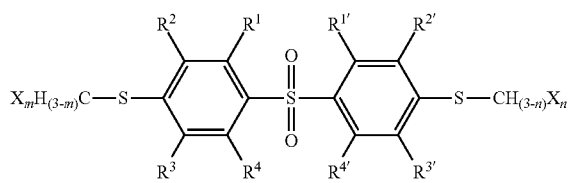

wherein $R^1$ to $R^4$, $R^{1'}$ to $R^{4'}$, X, m, and n are as defined above, is hydrolyzed, thereby obtaining the dimercaptodiaryl sulfone compound represented by Formula (2):

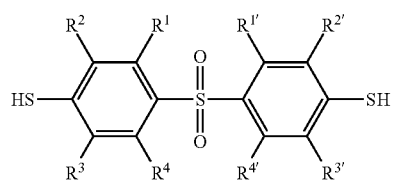

wherein $R^1$ to $R^4$ and $R^{1'}$ to $R^{4'}$ are as defined above.

As the reaction solvent, a solvent obtained by adding water to the organic solvent used in the above halogenation reaction can be used. Examples thereof include solvent mixtures consisting of water and polar solvents such as dimethylsulfoxide, N-methylpyrrolidone, N,N-dimethylformamide, and the like; solvent mixtures of water and halogenated hydrocarbons such as methylene chloride, 1,2-dichloroethane, chlorobenzene, and o-dichlorobenzene; solvent mixtures of water and hydrocarbons such as n-hexane, n-heptane, cyclohexane, toluene, xylene; and the like. In this case, a solvent mixture of a polar solvent and water is a homogeneous solvent, and a solvent mixture of halogenated hydrocarbon or hydrocarbon and water is a biphasic solvent. A biphasic solvent of toluene and water is particularly preferable from an economic viewpoint.

The amount of water used for hydrolysis is preferably about 2 to 200 mol, more preferably about 10 to 50 mol, per mole of the diaryl sulfone compound.

The reaction temperature is preferably about 30 to 150° C., and preferably about 70 to 120° C. The reaction time is usually about 1 to 30 hours.

The dimercaptodiaryl sulfone compound represented by Formula (2) can be obtained by the above-described method.

In the case where a biphasic solvent was used, the resulting dimercaptodiaryl sulfone compound can be obtained by distilling off the solvent after the organic layer and the aqueous layer are separated by liquid-liquid separation and the organic phase is washed with water. In the case where a homogeneous solvent was used, the dimercaptodiaryl sulfone compound can be easily obtained by a method such as filtration.

Specific examples of the diaryl sulfone compound obtained in the present invention include 4,4'-dimercaptodiphenyl sulfone, and the like.

(3) Method for Producing Dimethylthiodiaryl Sulfone Compound

The dimethylthiodiaryl sulfone compound used in the above-described step of reacting the dimethylthiodiaryl sulfone compound with a halogenating agent, and represented by Formula (6):

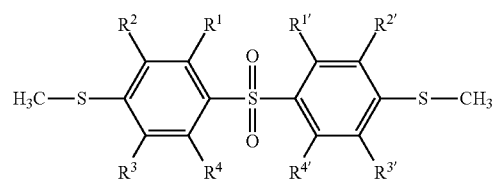

wherein $R^1$ to $R^4$ and $R^{1'}$ to $R^{4'}$ are the same or different, and each represents hydrogen, $C_{1-4}$ alkyl, or halogen, is a novel compound, and can be obtained, for example, by the following method.

For example, a 4,4'-dihalodiaryl sulfone compound represented by the following Formula (8):

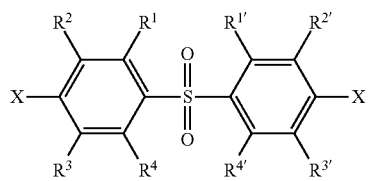

wherein $R^1$ to $R^4$ and $R^{1'}$ to $R^{4'}$ are the same or different; each represents hydrogen, $C_{1-4}$ alkyl, or halogen; and X represents halogen,
is reacted with a thiol salt compound represented by Formula (9): $MSCH_3$ wherein M represents an alkali metal. In this way, the compound represented by the above Formula (6) can be obtained.

The 4,4'-dihalodiaryl sulfone compound of Formula (8) used as a starting material is a known compound and is a relatively less-expensive substance. In Formula (8), examples of the halogen represented by X include chlorine, bromine, iodine, and the like, with chlorine being particularly preferable.

Specific examples of each of the groups represented by $R^1$ to $R^4$ and $R^{1'}$ $R^{4'}$ are the same as those in Formula (1).

Examples of the alkali metal represented by M in the thiol salt compound of the above Formula (9) include sodium, potassium, lithium, and the like.

Specific examples of the thiol salt compound of Formula (9) include sodium methanethiolate and the like.

The thiol salt compound of Formula (9) may be directly added as an alkali metal salt to the reaction solvent; or thiol represented by Formula: $HSCH_3$ and an alkali metal hydride (MH) or an alkali metal hydroxide (MOH) may be added to the solvent so as to form a salt in the solvent.

The amount of the thiol salt compound of Formula (9) used is preferably about 2 to 6 mol, more preferably about 2 to 3 mol, per mole of the 4,4'-dihalodiaryl sulfone compound of Formula (8).

Preferably, the reaction of the 4,4'-dihalodiaryl sulfone compound represented by Formula (8) with the thiol salt compound represented by Formula (9) is performed in a polar solvent such as dimethylsulfoxide, N-methylpyrrolidone, or N,N-dimethylformamide, or in a biphasic solvent of water and an organic solvent such as a halogenated hydrocarbon (e.g., methylene chloride, 1,2-dichloroethane, chlorobenzene, or o-dichlorobenzene) or a hydrocarbon (e.g., n-hexane, n-heptane, cyclohexane, toluene, xylene, or the like). From an economic viewpoint, use of N-methylpyrrolidone alone or a biphasic solvent of toluene and water is particularly preferable.

When a polar solvent is used, the reaction solvent is preferably used in an amount of about 10 to 5,000 parts by weight, more preferably about 100 to 1000 parts by weight, relative to 100 parts by weight of the 4,4'-dihalodiaryl sulfone compound represented by Formula (8).

When a biphasic solvent is used, both organic solvent and water are preferably used in an amount of about 10 to 5,000 parts by weight, more preferably about 100 to 1,000 parts by weight, relative to 100 parts by weight of the 4,4'-dihalodiaryl sulfone compound represented by Formula (8).

When the reaction is carried out in a biphasic solvent, it is preferable to use a phase-transfer catalyst. Examples of phase-transfer catalysts that can be used include quaternary ammonium salts such as benzyltriethylammonium bromide, benzyltrimethylammonium bromide, dodecyltrimethylammonium chloride, tetra-n-butylammonium bromide, tetraethylammonium bromide, and trioctylmethylammonium bromide; quaternary phosphonium salts such as hexadodecyltriethylphosphonium bromide, hexadodecyltributylphosphonium chloride, and tetra-n-butylphosphonium chloride; and the like. Tetra-n-butylammonium bromide is particularly preferable in view of the increased yield and the economic efficiency.

The amount of phase-transfer catalyst used is preferably about 0.1 to 100 parts by weight, more preferably about 0.1 to 10 parts by weight, relative to 100 parts by weight of the 4,4'-dihalodiaryl sulfone compound of Formula (8).

The reaction temperature is preferably about 30 to 150° C., and more preferably about 60 to 150° C. The reaction time is usually about 1 to 30 hours.

The specific reaction method is not particularly limited. Usually, a catalyst is added, if necessary, to the above-described solvent, and the 4,4'-dihalodiaryl sulfone compound represented by Formula (8) and the thiol salt compound represented by Formula (9) are uniformly mixed in the solvent. The order of addition of each component is not particularly limited, and any method can be employed.

The diaryl sulfone compound represented by Formula (6):

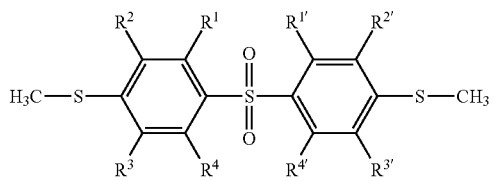

wherein $R^1$ to $R^4$ and $R^{1'}$ to $R^{4'}$ are as defined above; can be produced by the above-described method.

The resulting diaryl sulfone can be obtained, if necessary, by water-washing and liquid-liquid separation. The diaryl sulfone compound can also be isolated with high purity by recrystallization after distilling off the solvent.

Advantageous Effects of Invention

According to the method of the present invention, the desired diaryl sulfone compound can be obtained with a good yield with a relatively simple production process, using the 4,4'-dimercaptodiaryl sulfone compound represented by Formula (2), which is an inexpensive substance, as a starting material.

The diaryl sulfone compound obtained by this method is a useful compound as a monomer that is used for producing synthetic resin for optical materials having a high refractive index and good transparency, and can be effectively used as a raw material for optical materials, such as plastic lenses for glasses, fresnel lens, lenticular lens, optical disk bases, and plastic optical fibers.

The 4,4'-dimercaptodiaryl sulfone compound represented by the above Formula (2) used as a starting material in the above method can be simply produced with a less expensive process by the production method of the present invention.

DESCRIPTION OF EMBODIMENTS

The present invention is described in further detail below with reference to examples.

Example 1

Production of Bis[(4-glycidylthio)phenyl]sulfone 4,4'-Dimercaptodiphenyl sulfone (9.88 g, 35.0 mmol), lithium chloride (0.07 g, 1.8 mmol), toluene (20.00 g), and methanol (10.00 g) were placed in a 100 mL-flask equipped with a stirrer, a thermometer, a condenser, and a gas inlet tube. Subsequently, the temperature of the solution was raised to 50° C., and epichlorohydrin (6.70 g, 72.0 mmol) was added thereto. The reaction was carried out under stirring at 50° C. for 2 hours.

After the reaction was completed, the temperature of the solution was cooled to 30° C., and water (9.8 g), 50% by weight of tetrabutylammonium bromide (1.0 g), and 30% by weight aqueous solution of sodium hydroxide (9.70 g, 72.8 mmol) were added thereto. The reaction was carried out under stirring at 35° C. for 1 hour.

After the reaction was completed, the oil layer was separated by liquid-liquid separation and the solvent was distilled off, thereby obtaining bis(4-oxiranylmethyl sulfanylphenyl) sulfone (11.05 g). The yield relative to bis[(4-glycidylthio) phenyl]sulfone was 80%.

$^1$H NMR d 2.65 (dd, J=2.4 Hz, 4.8 Hz, 2H), 2.83 (dd, J=3.6 Hz, 4.4 Hz, 2H), 3.15-3.21 (m, 6H), 7.41 (d, J=8.8 Hz, 4H), 7.80 (d, J=8.8 Hz, 4H);

Elemental analysis (as $C_{18}H_{18}O_4S_3$);
Calculated: C, 54.80%; H, 4.60%; O, 16.22%; S, 24.38%.
Found: C, 54.76%; H, 4.62%; O, 16.14%; S, 24.48%.
Refractive index: 1.645

Example 2

Production of Bis[(4-thioglycidylthio)phenyl]sulfone

Bis[(4-glycidylthio)phenyl]sulfone (6.00 g, 15.0 mmol), methylene chloride (23.40 g), and methanol (31.00 g) were placed in a 100 mL-flask equipped with a stirrer, a thermometer, a condenser, and a gas inlet tube. Subsequently, the temperature of the solution was raised to 45° C., and thiourea (9.10 g, 120.0 mmol) was added thereto. The reaction was carried out under stirring at 45° C. for 4 hours.

After the reaction was completed, water (37.00 g) was added to separate the oil layer by liquid-liquid separation, and the solvent was distilled off, thereby obtaining bis[(4-thioglycidylthio)phenyl]sulfone (5.79 g). The yield relative to bis[(4-glycidylthio)phenyl]sulfone was 89%.

$^1$H NMR d 2.23 (dd, J=1.2 Hz, 5.2 Hz, 2H), 2.83 (m, 2H), 2.94-3.21 (m, 6H), 7.41 (d, J=8.8 Hz, 4H), 7.82 (d, J=8.4 Hz, 4H);

Elemental analysis (as $C_{18}H_{18}O_2S_5$);
Calculated: C, 50.67%; H, 4.25%; O, 7.50%; S, 37.58%.
Found: C, 50.76%; H, 4.22%; O, 7.45%; S, 37.57%.
Refractive index: 1.664

Example 3

Production of Bis(4-acryloylthiophenyl)sulfone 4,4'-Dimercaptodiphenyl sulfone (1.95 g, 6.9 mmol) and 10% by weight aqueous solution of sodium hydroxide (6.00 g, 15.0 mmol) were placed in a 10 mL-flask equipped with a stirrer, a thermometer, a condenser, and a gas inlet tube. Subsequently, the temperature of the solution was cooled to 10° C. (reaction solution A). Meanwhile, acryloyl chloride (1.31 g, 14.5 mmol), cyclohexane (5.00 g), and toluene (2.00 g) were placed in a 25 mL-flask equipped with a stirrer, a thermometer, a condenser, and a gas inlet tube. The temperature of the solution was subsequently cooled to 10° C., and the reaction solution A was added dropwise thereto over a period of 30 seconds. The reaction was carried out under stirring at 20° C. for 1 hour.

After the reaction was completed, the reaction solution was filtered, thereby obtaining bis(4-acryloylthiophenyl)sulfone (1.08 g) as a white powder. The yield relative to 4,4'-dimercaptodiphenyl sulfone was 40%.

$^1$H NMR d 5.70 (d, J=9.2 Hz, 2H), 6.34-6.49 (m, 4H), 7.55 (d, J=6.8 Hz, 4H), 7.88 (d, J=6.8 Hz, 4H);

Elemental analysis (as $C_{18}H_{14}O_4S_3$);
Calculated C, 55.36%; H, 3.61%; O, 16.39%; S, 24.63%.
Found C, 55.28%; H, 3.58%; O, 16.43%; S, 24.70%.
Refractive index: 1.639

Example 4

Production of Bis(4-acryloylthiophenyl)sulfone 4,4'-Dimercaptodiphenyl sulfone (1.95 g, 6.9 mmol) and 10% by weight aqueous solution of sodium hydroxide (6.00 g, 15.0 mmol) were placed in a 10 mL-flask equipped with a stirrer, a thermometer, a condenser, and a gas inlet tube, and the temperature of the solution was cooled to 10° C. Subsequently, acryloyl chloride (1.31 g, 14.5 mmol) was added dropwise thereto over a period of 30 seconds. The reaction was carried out under stirring at 20° C. for 1 hour. After the reaction was completed, the reaction solution was filtered, thereby obtaining bis(4-acryloylthiophenyl)sulfone (0.95 g) as a white powder. The yield relative to 4,4'-dimercaptodiphenyl sulfone was 35%.

Example 5

Production of Bis(4-methacryloylthiophenyl)sulfone 4,4'-Dimercaptodiphenyl sulfone (1.95 g, 6.9 mmol) and 10% by weight aqueous solution sodium hydroxide (6.00 g, 15.0 mmol) were placed in a 10 mL-flask equipped with a stirrer, a thermometer, a condenser, and a gas inlet tube. Subsequently, the temperature of the solution was cooled to 10° C. (reaction solution A). Meanwhile, methacryloyl chloride (1.52 g, 14.5 mmol), cyclohexane (5.00 g), and toluene (3.00 g) were placed in a 25 mL-flask equipped with a stirrer, a thermometer, a condenser, and a gas inlet tube. The temperature of the solution was subsequently cooled to 10° C., and the reaction solution A was added dropwise thereto over a period of 30 seconds. The reaction was carried out under stirring at 20° C. for 1 hour.

After the reaction was completed, the reaction solution was filtered, thereby obtaining bis(4-methacryloylthiophenyl)sulfone (2.58 g) as a white powder. The yield relative to 4,4'-dimercaptodiphenyl sulfone was 90%.

$^1$H NMR d 2.00 (s, 6H), 5.77 (s, 2H), 6.21 (s, 2H), 7.60 (d, J=6.8 Hz, 4H), 7.98 (d, J=6.8 Hz, 4H);

Elemental analysis (as $C_{20}H_{18}O_4S_3$);
Calculated: C, 57.39%; H, 4.33%; O, 15.29%; S, 22.98%.
Found: C, 57.30%; H, 4.38%; O, 15.35%; S, 22.96%.
Refractive index: 1.631

Example 6

Production of Bis(4-methacryloylthiophenyl)sulfone 4,4'-Dimercaptodiphenyl sulfone (1.95 g, 6.9 mmol), sodium hydride (0.36 g, 15.2 mmol), and N-methylpyrrolidone (6.00 g) were placed in a 10 mL-flask equipped with a stirrer, a thermometer, a condenser, and a gas inlet tube, and the temperature of the solution was then cooled to 10° C. Subsequently, methacryloyl chloride (1.52 g, 14.5 mmol) was added dropwise thereto over a period of 30 seconds. The reaction was carried out under stirring at 20° C. for 1 hour. After the reaction was completed, water (5.0 g) was added to the reaction solution, and filtration was then performed, thereby obtaining bis(4-methacryloylthiophenyl)sulfone (2.44 g) as a white powder. The yield relative to 4,4'-dimercaptodiphenyl sulfone was 85%.

Example 7

Production of 4,4'-Dimercaptodiphenyl Sulfone 4,4'-Dimethylthiodiphenyl sulfone (8.4 g, 27 mmol) and toluene (50.0 g) were placed in a 100 mL-flask equipped with a stirrer, a thermometer, a condenser, and a gas inlet tube, and the temperature was raised. While the temperature of the solution was maintained at 75° C., chlorine gas (4.8 g, 68 mmol) was bubbled into the solution, and the reaction was carried out for 1 hour under stirring. As a result, bis(4-chloromethylsulfanylphenyl)sulfone was produced in the system.

Subsequently, water (20.0 g) was added thereto, the temperature of the solution was raised to 110° C. under stirring, and a hydrolysis reaction was carried out for 12 hours. After the reaction was completed, the temperature of the solution was cooled, and precipitated crystals were filtered, thereby obtaining 4,4'-dimercaptodiphenyl sulfone (6.9 g). The yield relative to 4,4'-dimethylthiodiphenyl sulfone was 90%.

Production Example 1

Production of 4,4'-Di(methylthio)diphenyl Sulfone 4,4'-Dichlorodiphenyl sulfone (61.0 g, 212 mmol), toluene (75.0 g) and 50% by weight aqueous solution of tetra-n-butylammonium bromide (1.0 g) were placed in a 300 mL-flask equipped with a stirrer, a thermometer, a condenser, and a gas inlet tube; and the temperature was raised. While the temperature of the solution was maintained at 60° C., 32% by weight aqueous solution of sodium methanethiolate (97.5 g, 445 mmol) was added dropwise to carry out the reaction for 5 hours under stirring.

After the reaction was completed, the temperature of the solution was cooled to 25° C., and filtration was performed, thereby obtaining 4,4'-di(methylthio)diphenyl sulfone.

Next, the obtained crude 4,4'-di(methylthio)diphenyl sulfone and acetonitrile (150.0 g) were placed in a 300 mL-flask equipped with a stirrer, a thermometer, a condenser, and a gas inlet tube, and dissolved by increasing the temperature of the solution to 80° C. After dissolution, the temperature of the solution was cooled to 10° C., and filtration was performed, thereby obtaining 4,4'-di(methylthio)diphenyl sulfone (62.5 g). The yield relative to 4,4'-dichlorodiphenyl sulfone was 95%.

$^1$H NMR d 2.48 (s, 6H), 7.27 (d, J=8.4 Hz, 4H), 7.79 (d, J=8.8 Hz, 4H);

Elemental analysis (as $C_{14}H_{14}O_2S_3$);
Calculated: C, 54.16%; H, 4.55%; O, 10.31%; S,30.99%.
Found: C, 54.19%; H, 4.61%; O, 10.27%; S, 30.94%.
Refractive index: 1.644

The invention claimed is:

1. A diaryl sulfone compound represented by Formula (1):

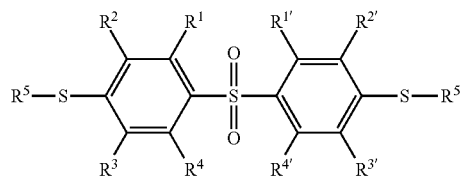

wherein $R^1$ to $R^4$ and $R^{1'}$ to $R^{4'}$ are the same or different, and each represents hydrogen, $C_{1-4}$ alkyl, or halogen; and $R^5$ is a group represented by the following formula:

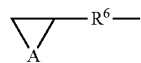

wherein $R^6$ represents $C_{1-4}$ alkylene, and A represents oxygen or sulfur;
or a group represented by the following formula:

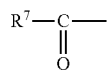

wherein $R^7$ represents $C_{2-5}$ alkenyl.

2. The diaryl sulfone compound according to claim 1, represented by Formula (1-1):

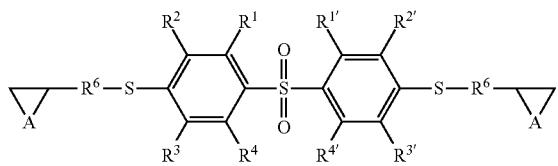

wherein $R^1$ to $R^4$ and $R^{1'}$ to $R^{4'}$ are the same or different, and each represents hydrogen, $C_{1-4}$ alkyl or halogen; $R^6$ represents $C_{1-4}$ alkylene; and A represents oxygen or sulfur.

3. The diaryl sulfone compound according to claim 1, represented by Formula (1-2):

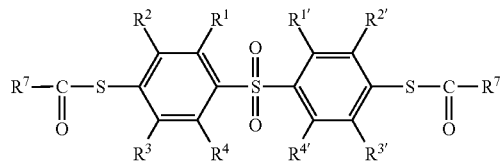

wherein $R^1$ to $R^4$ and $R^{1'}$ to $R^{4'}$ are the same or different, and each represents hydrogen, $C_{1-4}$ alkyl or halogen; and $R^7$ represents $C_{2-5}$ alkenyl.

4. The diaryl sulfone compound according to claim 1, wherein $R^1$ to $R^4$ and $R^{1'}$ to $R^{4'}$ are all hydrogen.

5. A method for producing a diaryl sulfone compound represented by Formula (1-1-a):

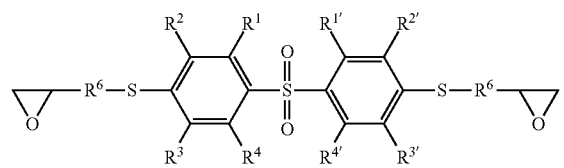

wherein $R^1$ to $R^4$ and $R^{1'}$ to $R^{4'}$ are the same or different, and each represents hydrogen, $C_{1-4}$ alkyl or halogen; and $R^6$ is $C_{1-4}$ alkylene;
the method comprising reacting a 4,4'-dimercaptodiaryl sulfone compound represented by Formula (2):

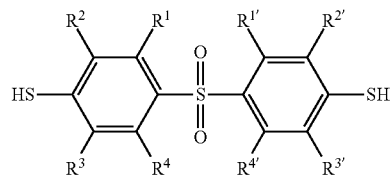

wherein $R^1$ to $R^4$, $R^{1'}$ to $R^{4'}$, and $R^6$ are as defined above;
with a halide represented by Formula (3):

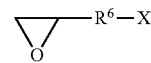

wherein $R^6$ is as defined above and X is halogen;
in a solvent in the presence of at least one catalyst selected from the group consisting of lithium chloride and lithium bromide to produce a compound represented by Formula (4):

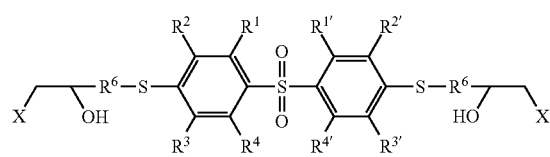

wherein $R^1$ to $R^4$, $R^{1'}$ to $R^{4'}$, $R^6$, and X are as defined above; and reacting the resulting compound with a base to perform a dehydrohalogenation reaction.

6. A method for producing diaryl sulfone compound represented by Formula (1-1-b):

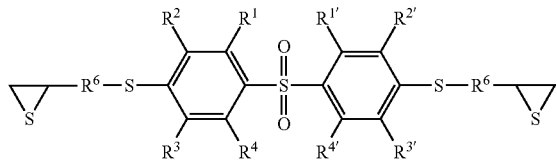

wherein $R^1$ to $R^4$ and $R^{1'}$ to $R^{4'}$ are the same or different, and each represents hydrogen, $C_{1-4}$ alkyl, or halogen; and $R^6$ represents $C_{1-4}$ alkylene;
the method comprising reacting a compound represented by Formula (1-1-a):

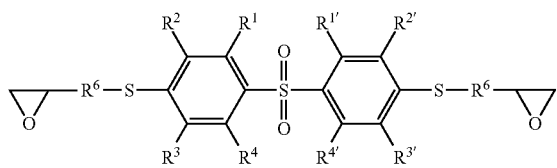

wherein $R^1$ to $R^4$, $R^{1'}$ to $R^{4'}$, and $R^6$ are as defined above;
with at least one compound selected from the group consisting of thiourea and thiocyanates, in an organic solvent.

7. A method for producing a diaryl sulfone compound represented by Formula (1-2):

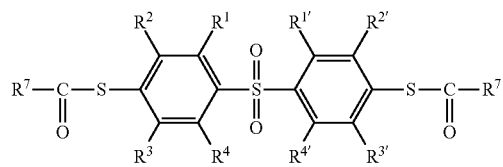

wherein $R^1$ to $R^4$ and $R^{1'}$ to $R^{4'}$ are the same or different, and each represents hydrogen, $C_{1-4}$ alkyl, or halogen; and $R^7$ represents $C_{2-5}$ alkenyl;
the method comprising reacting a salt of 4,4'-dimercaptodiaryl sulfone represented by Formula (2-1):

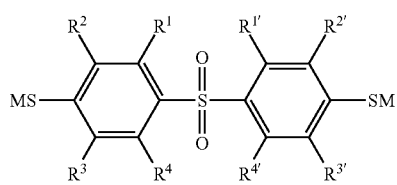

wherein $R^1$ to $R^4$, $R^{1'}$ to $R^{4'}$, and $R^7$ are as defined above; and M represents a cation moiety of a base;

with a halide represented by Formula (5):

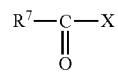

wherein $R^7$ is as defined above, and X represents halogen.

8. A method for producing a dimercaptodiaryl sulfone compound represented by Formula (2):

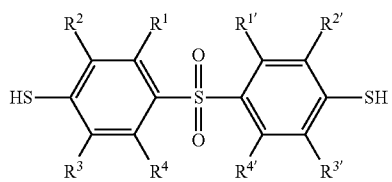

wherein $R^1$ to $R^4$ and $R^{1'}$ to $R^{4'}$ are the same or different, and each represents hydrogen, $C_{1-4}$ alkyl, or halogen;
the method comprising reacting a dimethylthiodiaryl sulfone compound represented by Formula (6):

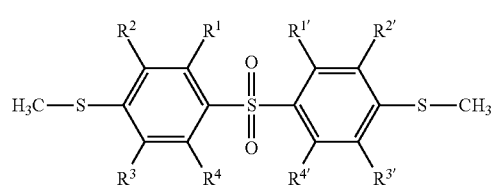

wherein $R^1$ to $R^4$ and $R^{1'}$ to $R^{4'}$ are as defined above;
with at least one halogenating agent selected from the group consisting of chlorine, sulfuryl chloride, phosphorus pentachloride, phosphorous trichloride, hypochlorous acid and bromine to obtain a diaryl sulfone compound represented by Formula (7):

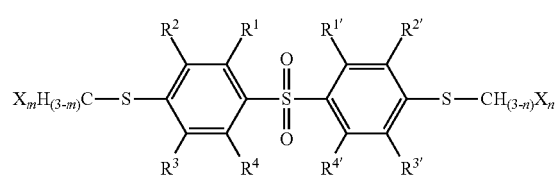

wherein $R^1$ to $R^4$ and $R^{1'}$ to $R^{4'}$ are as defined above; X represents halogen; and m and n each represents an integer of 1 to 3; and subjecting the resulting compound to hydrolysis.

9. The diaryl sulfone compound according to claim 2, wherein $R^1$ to $R^4$ and $R^{1'}$ to $R^{4'}$ are all hydrogen.

10. The diaryl sulfone compound according to claim 3, wherein $R^1$ to $R^4$ and $R^{1'}$ to $R^{4'}$ are all hydrogen.

* * * * *